Figure 1:
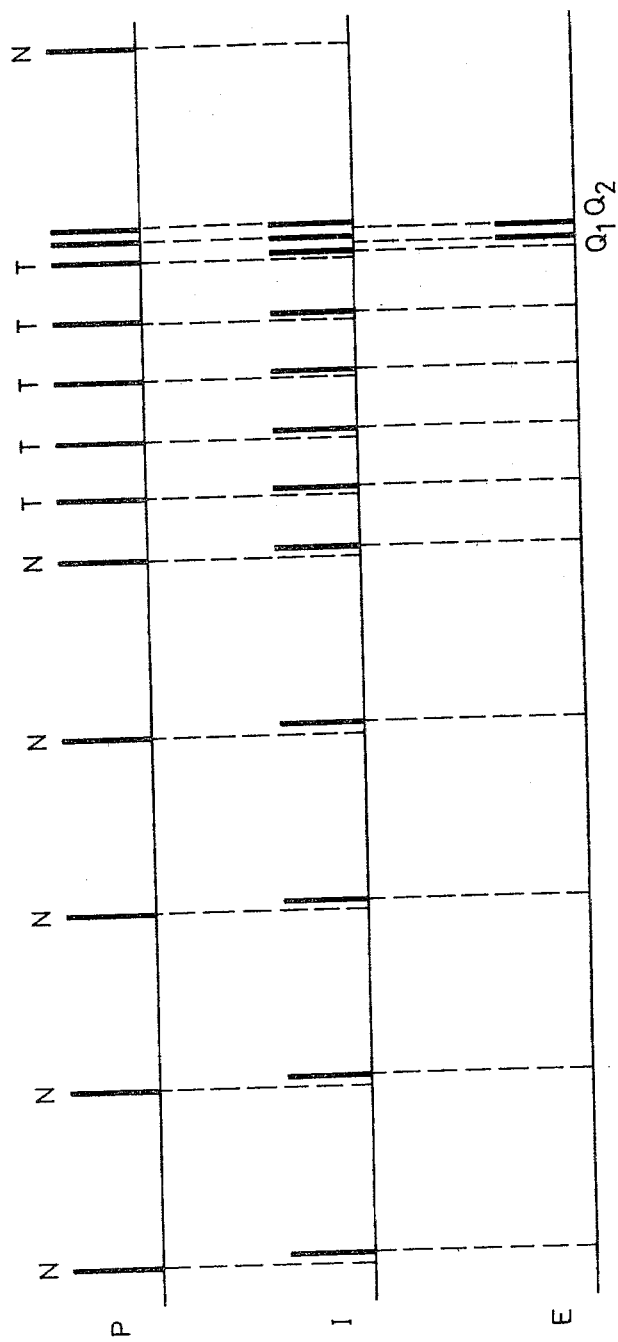

United States Patent [19]

Sowton et al.

[11] 4,307,725

[45] Dec. 29, 1981

[54] APPARATUS FOR TACHYCARDIA INVESTIGATION OR CONTROL

[75] Inventors: George E. Sowton, Sanderstead; John R. Smale, London, both of England; Jost L. Kappenberger, Zurich, Switzerland

[73] Assignee: Watfort Limited, England

[21] Appl. No.: 68,295

[22] Filed: Aug. 21, 1979

[30] Foreign Application Priority Data

Aug. 22, 1978 [GB] United Kingdom ............... 34206/78

[51] Int. Cl.³ ............................................. A61N 1/36
[52] U.S. Cl. ............................................. 128/419 PG
[58] Field of Search ...................... 128/419 D, 419 PG

[56] References Cited

U.S. PATENT DOCUMENTS

| | | | |
|---|---|---|---|
| 3,433,228 | 3/1969 | Keller, Jr. | 128/419 PG |
| 3,662,759 | 5/1972 | Dabolt | 128/419 PT |
| 3,683,934 | 5/1972 | Bukowiecki et al. | 128/419 PG |
| 3,881,493 | 5/1975 | Cannon | 128/419 PG |
| 4,088,140 | 5/1978 | Rockland et al. | 128/419 PG |

Primary Examiner—William E. Kamm
Attorney, Agent, or Firm—Steele, Gould & Fried

[57] ABSTRACT

An apparatus for the investigation and/or control of tachycardia comprising an implantable pacemaker having a short (typically 180 ms or lower) refractory period and providing in use, output pulses in response to external stimuli applied to the skin of the patient, and an external stimulus generator comprising means for generating the external stimuli. In the control of tachycardia, the implanted unit provides output pulses in response to natural heart beats. These output pulses are detected by the external stimulus generator through electrodes thereon held in contact with the skin. The external generator determines the pulse rate of the detected pulses and, if above a preset level, generates the external stimuli of an appropriate characteristic in time and number to cause the implanted unit to issue output pulses to arrest the tachycardia. The apparatus may also be used to induce a tachycardia, enabling non-invasive electrophysiological studies to be made.

9 Claims, 6 Drawing Figures

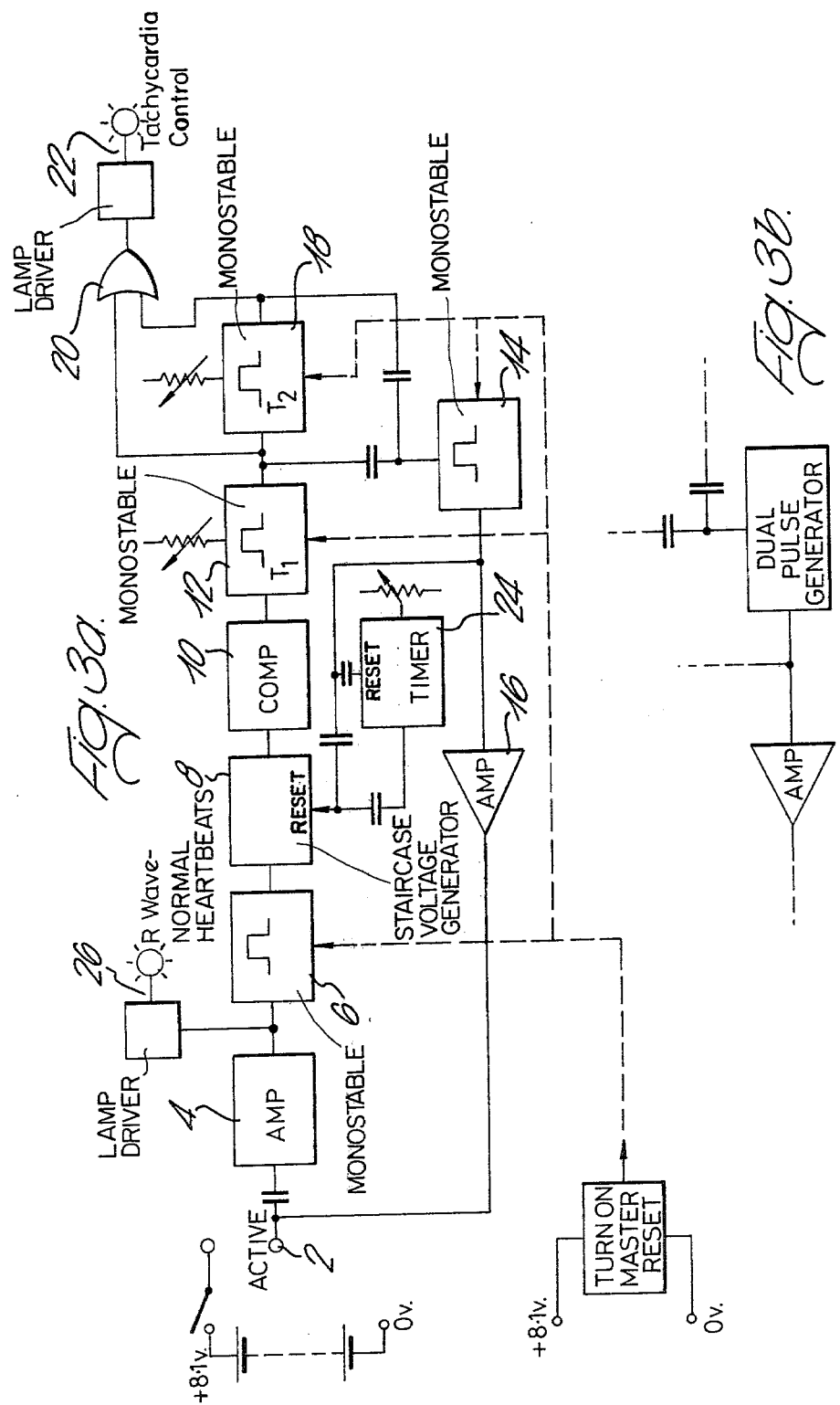

APPARATUS FOR TACHYCARDIA INVESTIGATION OR CONTROL

This invention relates to apparatus for control of tachycardia, or which enables repeated non-invasive electrophysiological studies of tachycardia to be conducted.

Tachycardia (abnormally rapid heart action) can be controlled by the application of external stimulation to the heart. Two main problems have however prevented the therapeutic use of such stimulation in non-hospital confined patients (i.e. outpatients). The first is that the known stimulus generators are too large and complicated to be implanted, and an external wire from the heart is generally unacceptable from a clinical viewpoint. Secondly, external sensing of the ECG to detect an arrhythmia is very difficult.

The present invention overcomes these problems by the employment of an implanted pacemaker working in combination with an external stimulus generator. The implanted pacemaker is normally triggered by the heart and provides output pulses in synchronism with the natural beats. These output pulses are detected by the external unit and their rate of generation determined. If the rate exceeds a predetermined level (indicating a tachycardia) then the external unit rapidly delivers a small number of appropriately-timed stimuli to the skin of the patient. These are not felt by the patient but are sensed by the implanted pacemaker which at once produces a small number of pulses causing premature contractions of the heart, thus terminating the tachycardia. To enable the pacemaker to respond to the stimuli provided by the external unit, its refractory (blocking) period is shorter than the period normally provided for pacemakers.

The principle thus described—the employment of an implanted pacemaker and an external stimulus controller—may also be used to enable repeated non-invasive electrophysiological studies of tachycardia to be conducted. The patient is supplied with an implanted pacemaker, which may for example include circuitry for controlling any cardiac arrhythmia, but additionally the pacemaker will include circuitry which enables it to be responsive to the external stimulus controller. When it is desired to study the patient's heart under tachycardia conditions, the external controller is employed to supply a series of appropriately-timed electrical pulses to the skin of the patient. These are sensed by the implanted unit and, in response thereto, the latter generates stimulating pulses to induce tachycardia artificially. The response of the heart to such conditions is then monitored in the usual manners. The timing of stimuli which start and stop tachycardia can be investigated by adjusting the timing of the pulses from the external controller. This arrangement thus avoids the need for an electrode to be inserted through the skin, as is customary with present electrophysiological investigations. Such parameters as refractory period can similarly be measured non-invasively.

According to the invention there is provided an apparatus for the investigation and/or control of tachycardia characterised by an implantable pacemaker having a short refractory period and providing, in use, output pulses in response to external stimuli applied to the skin of the patient, and an external stimulus generator comprising means for generating electrically said external stimuli, said pacemaker, in response to said external stimuli, generating stimulating pulses for either inducing an artificial tachycardia or for arresting a tachycardia either natural or induced.

The implantable pacemaker and the external stimulus generator themselves individually form separate aspects of the invention.

Preferably, the implantable pacemaker provides output pulses in response to natural heart beats, and the external generator includes circuitry for detecting such output pulses, for determining the pulse rate of said detected pulses, and for issuing said external stimuli when the detected pulse rate is above a predetermined level.

The implantable pacemaker may, for example, be of the ventricular-triggered type, such as that described in detail in U.S. Pat. No. 3,662,759, and the refractory period typically about 180 ms. or lower. Preferably the refractory period is no greater than 120 ms. All the output pulses provided may be of characteristic normally employed to stimulate the heart; alternatively, the pulses produced in response to natural heart beats may be "marker" pulses of short duration (of pulse-width insufficient to stimulate the heart, but sufficient to be detected by the external unit) with only the small number of tachycardia-controlling pulses being of characteristic to stimulate the heart. Preferably the pacemaker contains safety features to limit the number of tachycardia-controlling pulses produced. Typically one or two such pulses, delivered rapidly to the heart, are sufficient to terminate the tachycardia.

The external stimulus generator may be arranged to be permanently in contact with the patient's skin, and fully automatic, or it may be designed to be hand-held. In the latter case, for example, the unit may be carried, in, say, a pocket or bag by the patient. If the latter thinks that he (or she) has a tachycardia he places his hands on electrodes on the unit. This action will switch the unit on; it will then detect pulses produced by the implanted unit, determine the pulse rate and, if necessary, deliver, via the electrodes, the small number of rapid pulses to enable the implanted pacemaker to control the tachycardia. Preferably the unit provides indications (e.g. by means of flashing lights) for each heart beat and for when a tachycardia has been recognised and appropriate controlling pulses delivered. If the patient continues to hold the controller, the determination of rate will be repeated and, if again above a preset limit, further tachycardia-controlling pulses will be issued.

When the apparatus is employed solely for the noninvasive investigation of tachycardia, the pacemaker is implanted, but the patient is not supplied with the external stimulus generator. The latter is retained by the medical practitioner responsible for the patient, and it is only employed when the patient returns to the clinic for investigation.

In practice, the apparatus will probably be used in any given patient both for controlling tachycardia in non-hospital environments and for enabling non-invasive investigations to be conducted when the patient returns to a clinical environment.

Figure 2A:
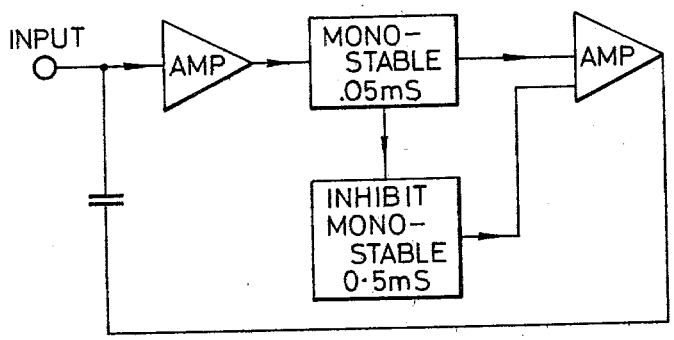
Figure 2B:
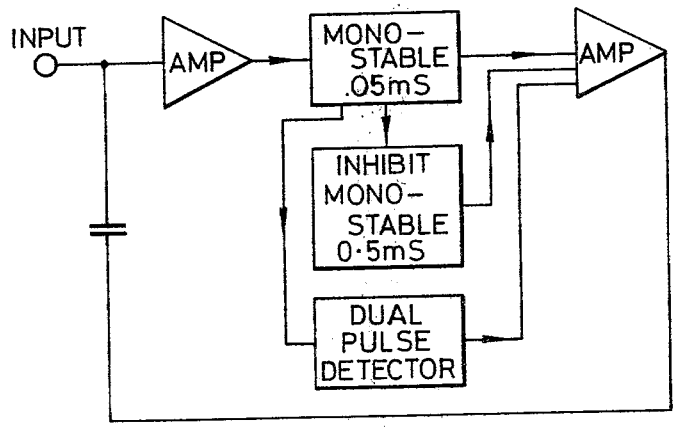
Figure 2C:
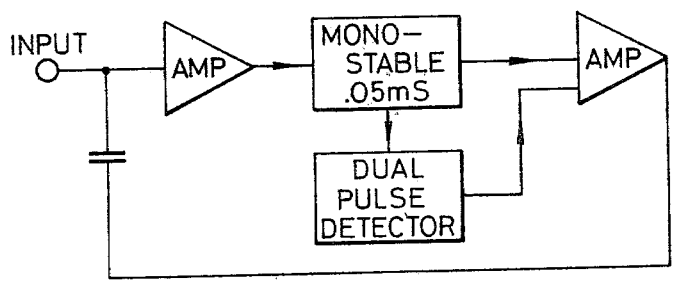

Preferred features of the invention are illustrated in the accompanying drawings, given by way of example wherein:

FIG. 1 is a pulse diagram to explain the principles of the invention, when employed to control naturally-occurring tachycardia, FIGS. 2 (a) (b) and (c) show schematically block circuit diagrams of three implanted pacemakers for use in the invention, when employed to control naturally-occurring tachycardia, and FIGS. 3 (a) and (b) show schematically block circuit diagrams of two external stimulus generators for use in the invention; the generator of FIG. 3 (a) being for use with the pacemaker illustrated in FIG. 2 (a) and the generator of FIG. 3 (b) being for use with the pacemaker illustrated in either FIG. 2 (b) or (c).

Referring to FIG. 1, which is merely schematic, the heart rhythm of the patient is shown in the row marked P. The output pulses produced by the implanted pacemaker are shown in the row marked I. The output pulses produced by the external stimulus generator are shown in the row marked E. As illustrated, the patient is initially in a normal heart condition, with beats at about, say, 70 per minute. These normal beats (pulses N) trigger the implanted unit which almost immediately issues corresponding output pulses. These pulses arise as the heart is depolarised and thus do not stimulate further heart contractions. When a tachycardia arises (pulses T), the pulse rate of the implanted unit increases correspondingly. This increase is detected by the external unit over a period of time and, if the rate is over a preset level, it rapidly issues two output pulses ($Q_1$, $Q_2$) to the patient's skin. These trigger the implanted unit, as described, and the two pacemaker pulses cause rapid contraction of the heart to terminate the tachycardia. This cycle of pulse rate determination etc. is repeated for as long as the external unit is switched on and is in contact with the skin.

Referring to FIG. 2 (a), there is illustrated in simplified block diagram form a standard triggered demand pacemaker having a reduced refractory period (about 180 ms). A more precise description of such a pacemaker may be found in U.S. Pat. No. 3,662,759. This triggers immediately on receipt of signals corresponding to heart beats or to signals from an external stimulus generator. In the presence of a tachycardia it responds to signals from the external unit (FIG. 3(a), see below). Additionally, it detects the presence of bradycardia (slow heart beats) and provides normal demand pacing facilities in the usual manner. All output pulses are typically 0.5 ms in width. As is already known, and illustrated in U.S. Pat. No. 3,433,228, an electronic blocking time may be used to stimulate or provide for the refractory period. As is also known, any a.c. amplifier will "block" for a time after a large signal is applied to the input.

Referring to FIG. 2(b), there is illustrated a triggered demand pacemaker, of reduced refractory period, normally providing short (e.g. 50 $\mu$sec) marker pulses during normal heart action and providing typically 0.5 ms pulses during bradycardia or tachycardia. Additionally, the pacemaker includes a dual pulse detector so as to provide the rapid tachycardia-controlling output pulses only in response to pairs of pulses of specific characteristics issued by the external unit. When the external unit (FIG. 3(b), see below) detects a tachycardia, it issues not single pulses $T_1$, and $T_2$ but two pairs of pulses, one pair for each of $T_1$ and $T_2$. The pacemaker responds only to these pairs of pulses to issue the tachycardia-controlling stimulating pulses to the heart.

Referring to FIG. 2 (c), there is illustrated a triggered pacemaker, of reduced refractory period providing short marker pulses and longer e.g. (0.5 ms) tachycardia-controlling pulses. The pacemaker has no demand facility and thus is suitable only for patients with tachycardia but no bradycardia. As with the FIG. 2 (b) pacemaker it has a dual pulse detector and is responsive only to pairs of input pulses of particular characteristics. This pacemaker can also be employed with the FIG. 3 (b) external unit.

FIG. 3 (a) shows one version of the external stimulus generator. The generator, when switched on and reset, is responsive to input pulses (derived from the implanted pacemaker by contact with the skin) at an active electrode 2. These pulses are amplified at 4 and employed to trigger a monostable 6. The monostable pulses feed a diode pump 8 which, with successive monostable pulses, acts as a staircase voltage generator. The output of the diode pump is supplied to a comparator 10 and, if over a preset level, a signal is supplied by the latter to fire a monostable 12. This monostable (which essentially generates the $Q_1$ pulse, FIG. 1) triggers an output monostable 14, the pulse from which is amplified (16) before being supplied to electrode 2 for transmission through the skin of the patient. Monostable 12 also triggers a second monostable 18 which, via monostable 14 and amplifier 16, generates the $Q_2$ pulse of FIG. 1). The signals from monostables 12 and 18 are supplied via an OR gate 20 to a lamp circuit 22, which gives a visual indication that tachycardia-controlling pulses are being generated by the unit. The heart rate at which the unit produces the pulses $T_1$, $T_2$ is determined by timer 24 which, after a preset time, resets diode pump 8. Thus, unless the staircase voltage generated by the diode pump within this preset time exceeds the comparison voltage in comparator 10, the unit is reset and no tachycardia-producing pulses are generated. Lamp circuit 26 provides an indication of normal heart beats.

The monostables 12 and 18 are shown schematically connected to polentiometers which can be employed to vary the timing of the pulses applied to the heart. These polentiometers would be preset for the patient by the medical practitioner, but may be employed to vary the timing if the unit is employed in non-invasive investigations as already described.

Referring to FIG. 3 (b), the external unit is identical to that shown in FIG. 3 (a) except that, in place of the monostable 14, a dual pulse generator 30 is supplied. This provides, for each pulse from 12 or 18, a pair of closely-spaced pulses of characteristics suitable to be detected by the implanted pacemaker of FIG. 2 (b) or (c). The provision of such "coded" signals provides better protection of the units against interference. Typically the pulses in each pair are of 50 $\mu$sec in duration and spaced by 2 ms.

It will be appreciated that there are many other ways of coding the output of the controller which can be recognised suitably for the implant.

We claim:

1. An apparatus for selectively investigating and controlling tachycardia, comprising:
    an implantable pacemaker having a short refractory period and having means for producing output pulses in response to both natural heartbeats and external stimuli applied to the skin of an implant patient, heart stimulating pulses being produced in response to the external stimuli; and,
    an external stimulus generator having means for generating electrically said external stimuli, said pacemaker, in response to said external stimuli, generating heart stimulating pulses for selectively inducing an artificial tachycardia and for arresting a tachycardia, whether natural or induced.

2. An apparatus according to claim 1, wherein the refractory period is not greater than 180 ms.

3. An apparatus according to claim 2, wherein the refractory period is not greater than 120 ms.

4. An apparatus according to claim 1, wherein the external generator includes circuitry for detecting the output pulses of the pacemaker produced in response to natural heartbeats and for issuing said external stimuli in response to the rate of said detected output pulses.

5. An apparatus according to claim 4, wherein the external generator comprises means for determining the pulse rate of said detected pulses and for generating said external stimuli when the determined pulse rate is above a predetermined level.

6. The apparatus of claims 1 or 4, wherein the output pulses produced in response to the natural heartbeats are marker non-stimulating, but detectable pulses for synchronizing the external stimulus generator.

7. The apparatus of claim 1, wherein the external stimulus generator further comprises means for producing coded pulses in multiples of at least two; and, the implantable pacemaker further comprises means for detecting the coded pulses, and for producing corresponding multiple heart stimulating pulses in response thereto.

8. An implantable pacemaker for use with an external stimulus generator having a pulse rate detector, the pacemaker comprising:
   means for producing detectable, nonstimulating output marker pulses in response to natural heartbeats; and
   means for producing heart stimulating pulses only in response to external stimuli from the external stimulus generator applied to the skin of an implant patient, whereby tachycardia can be selectively induced and arrested.

9. An external stimulus generator for use with an implantable pacemaker, the pacemaker producing detectable, non-stimulating output marker pulses in response to natural heartbeats and heart stimulating pulses in response to external stimuli applied to the skin of an implant patient, the external stimulus generator comprising:
   means for detecting the output marker pulses;
   means for determining the pulse rate of said detected marker pulses, a rate above a predetermined level indicating tachycardia;
   means for automatically generating said external stimuli when the determined pulse rate is above the predetermined level, whereby tachycardia may be automatically arrested; and,
   means for generating said external stimuli in response to manual control, whereby tachycardia may also be selectively induced and arrested.

* * * * *